US00PP22099P2

(12) United States Plant Patent
Bernuetz

(10) Patent No.: US PP22,099 P2
(45) Date of Patent: Aug. 30, 2011

(54) ***XEROCHRYSUM* PLANT NAMED 'BONDRELAIPI'**

(50) Latin Name: *Xerochrysum bracteatum*
Varietal Denomination: Bondrelaipi

(75) Inventor: Andrew Bernuetz, Silverdale (AU)

(73) Assignee: Bonza Botanicals Pty., Ltd., Yellow Rock NSW (AU)

( * ) Notice: Subject to any disclaimer, the term of this patent is extended or adjusted under 35 U.S.C. 154(b) by 0 days.

(21) Appl. No.: 12/924,191

(22) Filed: Sep. 22, 2010

(51) Int. Cl.
*A01H 5/00* (2006.01)

(52) U.S. Cl. ..... Plt./359

(58) Field of Classification Search ..... Plt./359
See application file for complete search history.

*Primary Examiner* — Kent L Bell
(74) *Attorney, Agent, or Firm* — Audrey Charles

(57) ABSTRACT

A new and distinct cultivar of *Xerochrysum* plant named 'Bondrelaipi', characterized by its double-type, pink and white bicolored inflorescences, dark green-colored foliage, and moderately vigorous, compact-mounded growth habit, is disclosed.

1 Drawing Sheet

Latin name of genus and species of plant claimed: *Xerochrysum bracteatum.*

Variety denomination: 'Bondrelaipi'.

BACKGROUND OF THE INVENTION

The present invention relates to a new and distinct cultivar of *Xerochrysum* plant botanically known as *Xerochrysum bracteatum* and hereinafter referred to by the cultivar name 'Bondrelaipi'.

The new cultivar originated in a controlled breeding program in Yellow Rock, New South Wales, Australia during December 2005. The objective of the breeding program was the development of *Xerochrysum* cultivars with large inflorescences having attractive colors, and moderately vigorous, compact-mounded growth habit.

The new *Xerochrysum* cultivar is the result of cross-pollination. The female (seed) parent of the new cultivar is the proprietary *Xerochrysum bracteatum* breeding selection designated 05-15, not patented, characterized by its double-type, pink and white bicolored inflorescences, dark green-colored foliage, low vigor, and compact-mounded growth habit. The male (pollen) parent of the new cultivar is the proprietary *Xerochrysum bracteatum* breeding selection designated 05-8, not patented, characterized by its double-type, white-colored inflorescences, dark green-colored foliage, and moderately vigorous, compact-mounded growth habit. The new cultivar was discovered and selected as a single flowering plant within the progeny of the above stated cross-pollination during August 2006 in a controlled environment at Yellow Rock, New South Wales, Australia.

Asexual reproduction of the new cultivar by terminal stem cuttings since August 2006 at Yellow Rock, New South Wales, Australia, Arroyo Grande, Calif., and West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Bondrelaipi' as a new and distinct cultivar of *Xerochrysum* plant:

1. Double-type, pink and white bicolored inflorescences;
2. Dark green-colored foliage; and
3. Moderately vigorous, compact-mounded growth habit.

Plants of the new cultivar differ from plants of the female parent primarily in growth vigor and from plants of the male parent primarily in inflorescence color.

Of the many commercially available *Xerochrysum* cultivars, the most similar in comparison to the new cultivar is Mohave Dark Rose 'KLEBB05351', U.S. Plant Pat. No. 18,490. However, in side by side comparisons, plants of the new cultivar differ from plants of 'KLEBB05351' in at least the following characteristics:

1. Plants of the new cultivar have an involucral bract color that is lighter than plants of 'KLEBB05351'; and
2. Plants of the new cultivar have fewer inflorescences than plants of 'KLEBB05351'.

BRIEF DESCRIPTION OF THE PHOTOGRAPHS

The accompanying photographs show, as nearly true as it is reasonably possible to make the same in color illustrations of this type, typical flower and foliage characteristics of the new cultivar.

Colors in the photographs differ slightly from the color values cited in the detailed description, which accurately describes the colors of 'Bondrelaipi'. The plants were grown in 4-inch pots for 9 weeks in a greenhouse at West Chicago, Ill.

DETAILED BOTANICAL DESCRIPTION

Figure 1:
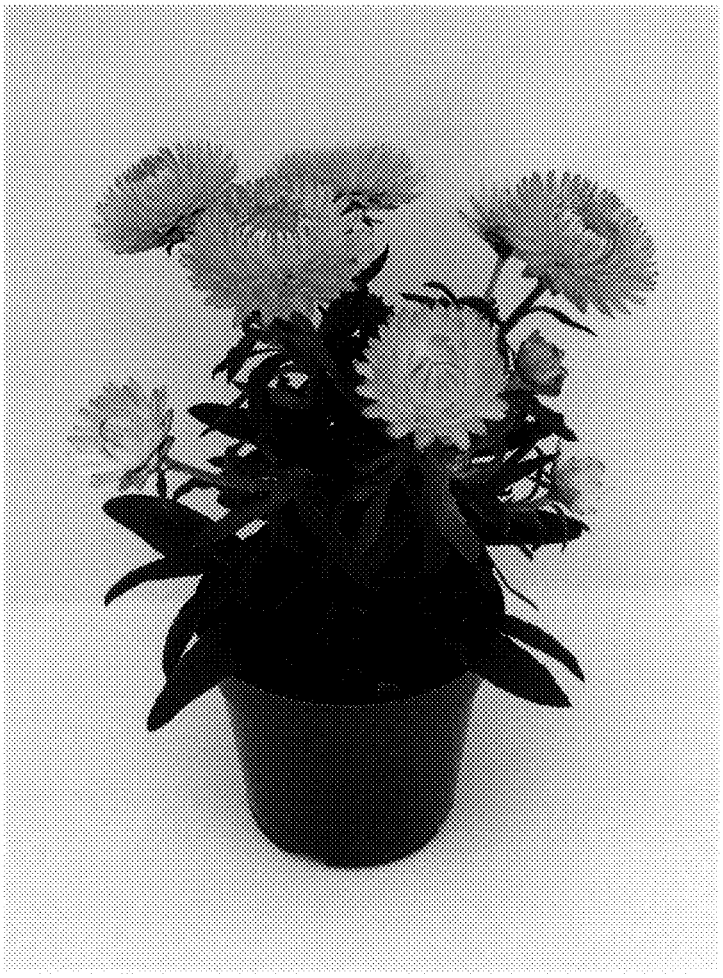
FIG. 1 illustrates a side view of the overall growth and flowering habit of 'Bondrelaipi'.
Figure 2:
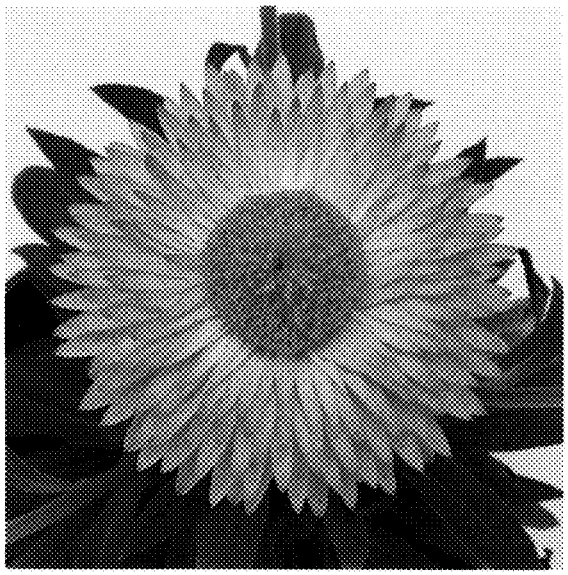
FIG. 2 illustrates a close-up view of an individual inflorescence of 'Bondrelaipi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined in July 2010 under natural light conditions in West Chicago, Ill.

The following descriptions and measurements describe plants produced from cuttings from stock plants and grown in a glass-covered greenhouse under conditions comparable to those used in commercial practice. The plants were grown in West Chicago, Ill. in 4-inch pots for 9 weeks utilizing a soilless growth medium. Greenhouse temperatures were maintained at approximately 70° F. to 77° F. (21° C. to 25° C.) during the day and approximately 65° F. to 68° F. (18° C. to 20° C.) during the night. Greenhouse light levels of 2,500 footcandles to 6,000 footcandles were maintained during the day. Measurements and numerical values represent averages of typical plants.

Botanical classification: *Xerochrysum bracteatum* cultivar Bondrelaipi.

Parentage:

*Female parent.*—*Xerochrysum bracteatum* breeding selection designated 05-15, not patented.

*Male parent.*—*Xerochrysum bracteatum* breeding selection designated 05-8, not patented.

Propagation:

*Type cutting.*—Terminal stem.

*Time to initiate roots.*—Approximately 6 to 9 days.

*Time to produce a rooted cutting.*—Approximately 21 to 28 days.

*Root description.*—Fibrous, fine.

*Rooting habit.*—Freely branching.

Plant description:

*Commercial crop time.*—Approximately 6 to 8 weeks from a rooted cutting to finish in a 10 cm pot.

*Growth habit and general appearance.*—Moderately vigorous, compact-mounded.

*Size.*—Height from soil level to top of plant plane: Approximately 16.7 cm. Width: Approximately 17.0 cm.

*Branching habit.*—Freely branching. Quantity of main branches per plant: Approximately 6.

*Branch.*—Strength: Strong. Length to base of peduncle: Approximately 4.2 cm. Diameter: Approximately 3.0 mm. Length of central internode: Approximately 4.0 mm. Texture: Densely pubescent. Color of young and mature stems: 144D.

Foliage description:

*General description.*—Quantity of leaves per main branch: Approximately 9. Fragrance: Slight. Form: Simple. Arrangement: Alternate.

*Leaves.*—Aspect: Acute angle to stem becoming downward turning with age. Shape: Linear to elliptic. Margin: Entire. Apex: Acuminate. Base: Sessile. Venation pattern: Parallel. Length of mature leaf: Approximately 8.1 cm. Width of mature leaf: Approximately 1.6 cm. Texture of upper surface: Moderately pubescent. Texture of lower surface: Sparsely pubescent. Color of upper surface of young foliage: 137A with indistinguishable venation except for midvien of 145B. Color of lower surface of young and mature foliage: Closest to 137B with indistinguishable venation except for midvien of 145B. Color of upper surface of mature foliage: Closest to 139A with indistinguishable venation except for midvien of 145B.

Flowering description:

*Flowering habit.*—'Bondrelaipi' is freely flowering under outdoor growing conditions with substantially continuous blooming from spring through autumn and year-round in greenhouse environment.

*Lastingness of individual inflorescence on the plant.*—Approximately 2 to 3 weeks.

Inflorescence description:

*General description.*—Type: Double, composite. Persistent. Shape: Hemispherical when involucral bracts are fully expanded. Aspect: Facing outward or upward held above the foliage. Arrangement: Terminal, solitary. Disc florets and involucral bracts develop acropetally on a capitulum. Fragrance: None. Quantity per plant: Approximately 4. Diameter: Approximately 5.6 cm. Depth: Approximately 2.7 cm.

*Peduncle.*—Strength: Strong. Aspect: Erect. Length: Approximately 6.9 cm. Diameter: Approximately 3.0 mm. Texture: Tomentose. Color: 144B.

*Bud.*—Rate of opening: Generally takes 14 to 21 days for bud to progress from first color to fully open flower. Quantity per plant: Approximately 6.

*Bud just before opening.*—Shape: Ovoid. Length: Approximately 1.5 cm. Diameter: Approximately 1.2 cm. Color: N155C.

*Involucral bracts.*—Quantity per inflorescence: Approximately 360. Arrangement: Imbricate in approximately 10 whorls. Aspect: Initially at acute angle to disc, becoming perpendicular at maturity and downward turning as senesce. Shape: Lanceolate, slightly cupped with sides turned upward. Margin: Entire. Apex: Acute. Base: Truncate. Length of outermost: Approximately 1.7 cm. Length of innermost: Approximately 8.0 mm. Width of outermost: Approximately 5.0 mm. Width of innermost: Approximately 1.0 mm. Texture of upper and lower surfaces: Glabrous, papery. Color of upper surface when first open: Purer white than 155D at base, gradually transitioning through 75D to 75C at tip, surface is spotted with 75C. Color of lower surface when first open: N155C. Color of upper surface when fully open: Purer white than 155D at base, gradually transitioning through 75C to N74D at tip, surface is spotted with N74D. Color of lower surface when fully open: Purer white than 155D at base, gradually transitioning through N155C to 75D at tip.

*Disc florets.*—Quantity per inflorescence: Numerous, greater than 800. Arrangement: Massed in center of inflorescence, multiple whorls of female florets at perimeter. Shape: Tubular with an outer whorl of approximately 20 pure-white, feather-like filaments, approximately 6.0 mm in length. Margin: Entire. Apex: Five acute tips. Base: Fused. Length: Approximately 1.2 cm. Diameter at apex: Approximately 1.0 mm. Diameter at base: Less than 1 mm. Texture: Glabrous. Color when fully open: 21A transitioning through 145D to a colorless, opaque base.

*Disc.*—Diameter: Approximately 2.1 cm. Depth: Approximately 1.5 cm.

*Receptacle.*—Shape: Flat. Diameter: Approximately 2.4 cm. Color: 145D.

*Reproductive organs.*—Androecium: Stamen quantity: 5 per floret, fused around the style. Stamen length: Approximately 9.0 mm. Anther shape: Linear. Anther length: Approximately 3.0 mm. Anther color: 14A.

Pollen amount: Moderate. Pollen color: 14B. Gynoecium: Pistil quantity: 1 per floret. Pistil length: Approximately 1.2 cm. Stigma shape: Bi-parted. Stigma length: Approximately 2.0 mm. Stigma color: 21A. Style length: Approximately 1.0 cm. Style color: Colorless, transparent. Ovary length: Approximately 1.0 mm. Ovary color: Colorless, opaque.

Seed and fruit production: Neither seed nor fruit production has been observed.

Disease and pest resistance: Resistance to pathogens and pests common to *Xerochrysum* has not been observed.

What is claimed is:

1. A new and distinct cultivar of *Xerochrysum* plant named 'Bondrelaipi', substantially as herein shown and described.

* * * * *